United States Patent [19]

Goodman et al.

[11] Patent Number: 4,826,966

[45] Date of Patent: May 2, 1989

[54] RADIOIODINATED BRANCHED CARBOHYDRATES

[75] Inventors: Mark M. Goodman, Knoxville; Furn F. Knapp, Jr., Oak Ridge, both of Tenn.

[73] Assignee: The United States of America as represented by the United States Department of Energy, Washington, D.C.

[21] Appl. No.: 175,798

[22] Filed: Mar. 31, 1988

Related U.S. Application Data

[62] Division of Ser. No. 857,230, Apr. 29, 1986.

[51] Int. Cl.$^4$ ............... C07H 15/00; A61K 49/02
[52] U.S. Cl. ............................ 536/18.4; 536/4.1; 536/18.2; 424/1.1
[58] Field of Search ................ 424/1.1; 536/4.1, 18.4, 536/18.5, 18.2

[56] References Cited

U.S. PATENT DOCUMENTS 3,843,626 10/1974 Sutton ................................. 536/4.1
4,439,414 3/1984 Shine et al. ......................... 424/1.1

OTHER PUBLICATIONS

Knapp, Jr. et al., "Radioiodinated Branched Carbohydrates" Nuclear Medicine Progress Report, Oak Ridge National Laboratory, 10/29/1985, pp. 12-20.
Knapp, Jr. et al., "Radioiodinated Branched Carbohydrates" Nuclear Medicine Progress Report, Oak Ridge National Laboratory, 5/1/85, pp. 8-11.

*Primary Examiner*—John S. Maples
*Attorney, Agent, or Firm*—Katherine P. Lovingood; Stephen D. Hamel; Judson R. Hightower

[57] ABSTRACT

A radioiodinated branched carbohydrate for tissue imaging. Iodine-123 is stabilized in the compound by attaching it to a vinyl functional group that is on the carbohydrate. The compound exhibits good uptake and retention and is promising in the development of radiopharmaceuticals for brain, heart and tumor imaging.

7 Claims, 1 Drawing Sheet

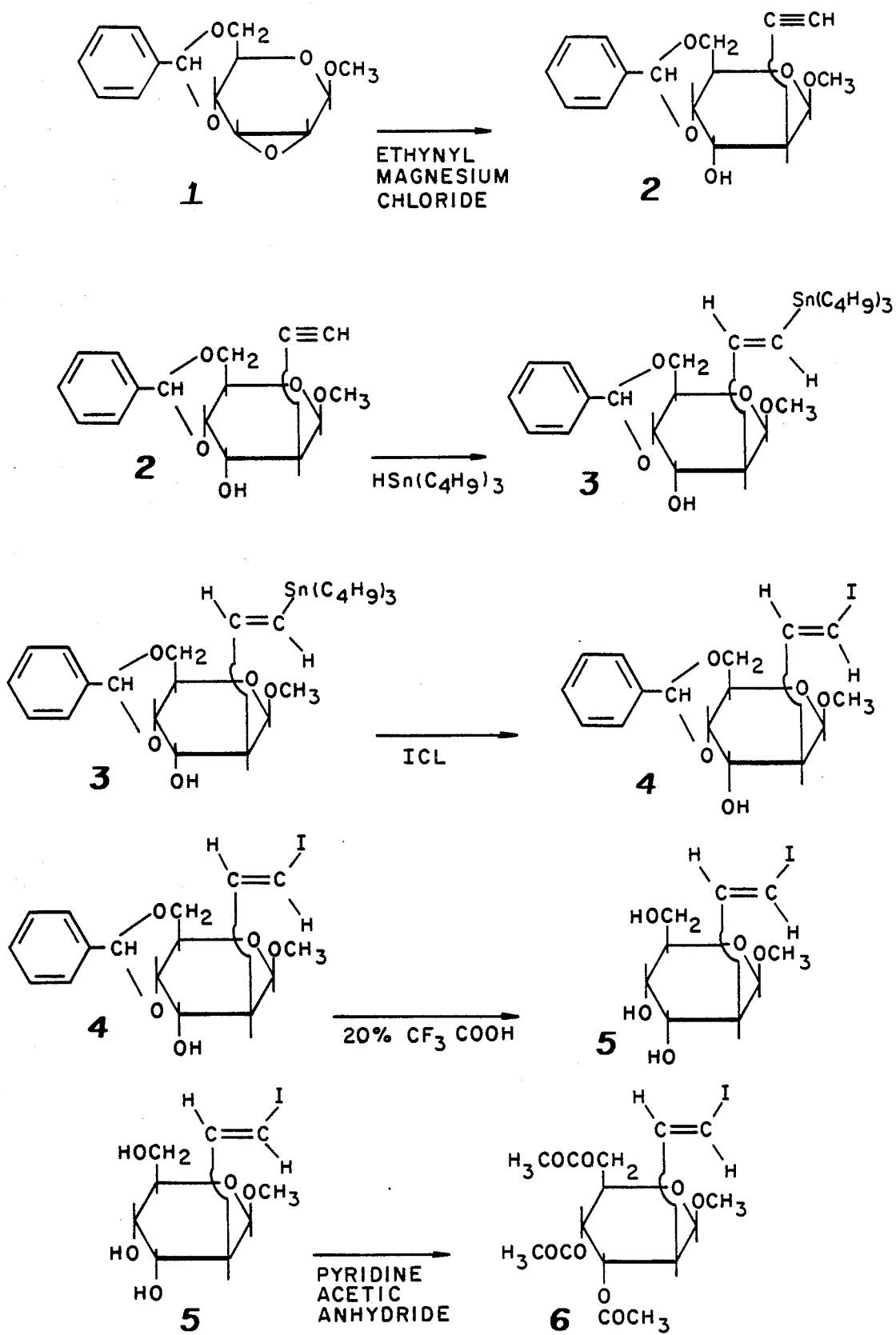

RADIOIODINATED BRANCHED CARBOHYDRATES

This is a division of application Ser. No. 857,230, filed Apr. 29, 1986.

This invention relates to a radiopharmaceutical in the form of a radioiodinated branched carbohydrate that can be used for brain, heart, and tumor imaging. This invention was prepared pursuant to a contract with the United States Department of Energy.

BACKGROUND OF THE INVENTION

Imaging of organs is a technique that utilizes a compound that is active in the body and which has been tagged with a radioactive element which can be detected using a special camera, the type camera being dependent upon the type of emissions from the radioactive element. This diagnostic tool is useful in studying reactions that take place in various body organs and can provide early detection of unusual reactions that can be indicative of disease. The chemical compound that carries the radioactive tag or label must travel through the organ that is being studied and must undergo a reaction that will provide information related to the state of health of the organ or the presence of a tumor. Glucose is the primary energy source of the brain and is also an important metabolic substrate for a normal heart and is therefore a good choice when selecting a vehicle to be tagged.

In the search for a suitable radiopharmaceutical for imaging purposes fluorine-18 has been used as a tag to form the compound fluoro-2-deoxy-D-glucose. Although the tagged compound is easily synthesized, fluorine-18 is available only from a cyclotron or reactor and it has a half-life of only 110 minutes; therefore, it is not readily available and its emissions are of limited duration. In addition to these problems, it also emits positrons having 511 keV gamma rays which cannot be detected using commonly available cameras. Considering their short half-lives, these compounds cannot be stored so they must be made, used, and measured at a single location, and since most hospitals do not have cyclotrons, reactors or special cameras for detecting the fluorine-18 compounds, this compound is not a practical choice for diagnostic purposes on a large scale. Another radioactive element, carbon-11, also would be easily incorporated into a glucose molecule; however, its half-life is only 20 minutes and it also emits 511 keV positrons.

A better choice is iodine-123 which emits particles having 159 keV that can be detected by all nuclear medicine imaging cameras, and since it also has a half-life of 13.3 hours, it can be stored for a longer period of time than can radioactive fluorine or carbon. However, use of iodine presents a problem because, due to its chemical properties, iodine is not easily attached to glucose or a glucose-like molecule. Therefore, there is a need to develop a process to synthesize iodine-123 tagged compounds which undergo reaction in desired organs or tumors in the body.

SUMMARY OF THE INVENTION

In view of the above need, it is an object of this invention to provide brain, heart, and tumor imaging agents that have long lives and are easy to detect using commonly available nuclear medicine imaging cameras.

It is another object of this invention to provide iodinated branched carbohydrates and a method for making them.

It is a further object of this invention to stabilize iodine on a carbohydrate so the compound does not become deiodinated in the body.

It is another object of this invention to provide a process for opening an epoxide ring using an unsaturated Grignard reagent. Other objects and advantages of this invention will become obvious to a person skilled in the art upon study of the specifications and the appended claims.

The invention is a composition of matter comprising a carbohydrate molecule to which is attached a vinyl functional group containing an iodine molecule.

The invention is also a process of opening an epoxide ring on a carbohydrate using an unsaturated Grignard reagent, wherein a selected carbohydrate is treated with ethynyl magnesium chloride.

In addition, the invention is a process for making a radioiodinated branched carbohydrate, wherein the first step is the breaking of the epoxide ring by the Grignard reagent. In a preferred embodiment, the product of this reaction is hydrostannylized with tributyl tin hydride. The product of this reaction was then iododestannylized with sodium iodide and N-chloro-succinimide, and the product of this reaction was hydrolized with 20 percent trifluoroacetic acid followed by a treatment with pyridine-Ac$_2$O resulting in the desired iodinated branched carbohydrate.

The invention is also a saline solution or other suitable administering medium containing any of the compounds of the above identified class in amounts sufficient to produce a distinct tissue image using radioimaging techniques.

The invention is also a process for radioimaging using a suitable solution containing a radioiodinated branched carbohydrate.

The compound that was prepared to test stability and activity showed favorable results when tested on the tissues of female rats and it is believed that this process and this compound constitute significant first steps in further development of effective imaging agents that can be easily manufactured and stored for a period of time and used in conjunction with conventional nuclear medicine imaging photography.

BRIEF DESCRIPTION OF THE DRAWING

A schematic drawing detailing the procedural steps and chemical intermediates of the process of making the compound described in the example of this invention.

DETAILED DESCRIPTION OF THE PREFERRED EMBODIMENT

In organ imaging, an element that emits radiation is tagged to a compound that travels through the body and enters the organ or area of the body which is the subject of investigation. For study of the brain, the heart, and tumors, glucose is a suitable carrier for the radioactive element since it feeds the brain as well as tumors and is also an important metabolic substrate for a normal heart. It is required for normal cerebral and myocardial metabolism; thus, the measurement of regional difference in uptake and clearance of a glucose-like compound carrying a radioactive tag could be an accurate and unique technique of detecting subtle differences in regional glucose metabolism that would correlate to the onset and progression of several forms of brain and heart disease.

Glucose enters the brain by crossing the blood-brain barrier; however, it cannot readily cross the barrier without assistance and thus requires an enzyme for transport. In theory, if a radioactive tag is placed on a compound that the enzyme will recognize as glucose, the enzyme will transport the radioactive compound across the blood-brain barrier. Fluorine-18 and carbon-11 can both easily be attached to a glucose-like compound since fluorine-18 is similar to a hydroxy group in size and electronegativity and carbon-11 can easily replace a nonradioactive carbon of the glucose molecule. However, when iodine-123 is chosen as a tag difficulties arise. Iodine has unfavorable chemical reactivity properties and is not easily attached to a glucose like compound; it also forms a weak carbon-iodine $sp^3$ bond, whereas both fluorine and carbon form strong sp3 carbon bonds. This weak bond of the iodine inhibits synthesis of a radiopharmaceutical and also promotes chemical as well as in vivo deiodination after synthesis.

One approach is to stabilize the iodine by changing the $sp^3$ bond to an $sp^2$ bond using a method that would not change the compound to such a great extent that the enzyme fails to recognize it as glucose. This invention provides a method of stabilizing an iodine by attaching it to a vinyl functional group attached to the carbohydrate while not affecting the carbohydrate to the extent that the enzyme does not recognize it and transport it across the blood-brain barrier. In this process, the vinyl group is first attached to the carbohydrate, and the iodine is subsequently attached to the vinyl functional group. In the course of preparing these compounds a new method was discovered of opening an epoxide ring using an unsaturated Grignard reagent in order to attach the vinyl functional group.

Glucose analogues were chosen as labeled gamma emitters in this experiment with the expectation that they would be transported across the blood-brain barrier into the brain and be active in the brain. It was hoped that once in the brain, the substituted glucose analogue would undergo a reaction which is the initial step of glycolysis. Ordinarily, the subsequent steps of glycolysis would follow; however, when the analogue containing a substituted iodine is used, subsequent enzymatic steps are inhibited resulting in prolonged cerebral retention of the radioactive compound. This allows measurement of the rate of the first step of glycolysis which is indicative of the health of the organ being studied. If the brain is being studied, then a decrease in the rate would indicate that the brain is not functioning properly. In the case of a tumor, the indication would be that the rate of reaction is excessive, leading to overactive growth in a particular area. The significance of the specific rates of activity in the glycolysis process would be apparent to those skilled in the art.

EXAMPLE

A test radiopharmaceutical methyl-2-deoxy-2-(E)-[$^{125}$I]-iodovinyl-2,4,6-O-triacetyl-$\beta$-D-altropyranoside 6 was prepared to establish that a deoxy substituted iodovinyl carbohydrate could be delivered to the brain in significant levels with prolonged retention. One novel aspect of the invention was the scission of an anhydro sugar with the Grignard reagent. This technique was chosen because a variety of 2-deoxy iodovinyl carbohydrates could be prepared depending on the position of the anhydro group within the pyranose ring. The process of the synthesis is shown in the drawing.

Methyl-2,3-anhydro-4,6-O-benzylidene-$\beta$-D-allopyranoside 1 was treated with ethynyl magnesium chloride to give 4,6-O-benzylidene-2-deoxy-2-ethynyl-$\beta$-D-altropyranoside 2. Ethynyl magnesium chloride (EMC) was placed in tetrahydrofuran, a solvent, to which was added the epoxide having a proportion to EMC of 1 to 10. This mixture was heated for four hours at reflux, subsequently cooled and added to water. The product was then extracted with ethyl ether, which was subsequently removed by evaporation in a vacuum. Final purification of the product was done by column chromatography to give compound 2. Hydrostannylation of 2 with tributyl tin hydride, n(Bu)$_3$-SnH, gave the key intermediate, methyl 4,6-O-benzylidene-2-deoxy-2-(E)-(n-Bu)$_3$SnHC=CH-$\beta$-D-altropyranoside 3. Iododestannylation of 3 with sodium iodide and N-chloro-succinimide gave methyl 4,6-O-benzylidene 2-deoxy-2-(E)-IHC=CH-$\beta$-D-altropyranoside 4. The processes of hydrostannylation and iododestannylation are described in the Journal of Medicinal Chemistry, Vol. 28, p.807, 1985. Hydrolysis of 4 with 20 percent trifluoroacetic acid, CF$_3$COOH, followed by treatment with pyridine-Ac$_2$O gave the desired radiopharmaceutical 6. These processes are commonly known to persons skilled in the art.

The distribution of radioactivity in tissues of female rats at 5 minutes, 15 minutes, 30 minutes and 60 minutes after intravenous administration of the iodinated compound is shown in the following table. The level of accumulation of radioactivity in the brain after injection of this agent was a significant 1.65 percent dose/g at 5 minutes but the blood levels were also high resulting in blood ratios of 1.6/1 at 5 minutes. The agent exhibited prolonged retention in the brain, 0.72 percent dose/g at 60 minutes which is 50 percent when compared with the peak uptake at 5 minutes. The accumulation of activity in the thyroid was low, 33.5 percent at 60 minutes, which demonstrated the stability of this agent to in vivo deiodination.

| Distribution of Radioactivity in Rat Tissues at Various Times after Intravenous Administration of [$^{125}$I]-Methyl-2-Deoxy-2-(E)~Iodovinyl-2,4,6-O~Triacetyl-$\beta$-D-Altropyranoside | | | | |
|---|---|---|---|---|
| | 5 MIN | 15 MIN | 30 MIN | 1 HT/R |
| Blood | 1.0549 | 0.9335 | 0.0037 | 0.6529 |
| Min | 1.00 | 0.089 | 0.74 | 0.64 |
| Max | 1.10 | 0.96 | 0.89 | 0.68 |
| S D | 0.0420 | 0.0371 | 0.0748 | 0.0266 |
| Liver | 1.3922 | 1.3676 | 1.2320 | 1.0541 |
| Min | 1.34 | 1.33 | 1.12 | 0.97 |
| Max | 1.42 | 1.39 | 1.42 | 1.10 |
| S D | 0.0380 | 0.0362 | 0.1620 | 0.0748 |
| Kidney | 1.5513 | 1.5725 | 1.6954 | 1.5722 |
| Min | 1.50 | 1.49 | 1.52 | 1.41 |
| Max | 1.59 | 1.63 | 1.84 | 1.74 |
| S D | 0.0351 | 0.0648 | 0.0674 | 0.0454 |
| Lung | 1.1948 | 1.0349 | 0.8325 | 0.6632 |
| Min | 1.09 | 0.97 | 0.74 | 0.66 |
| Max | 1.33 | 1.11 | 0.92 | 0.67 |
| S D | 0.1140 | 0.0710 | 0.0921 | 0.0051 |
| Thyroid | 20.6441 | 18.9149 | 25.7085 | 33.4920 |
| Min | 20.06 | 17.53 | 22.95 | 27.79 |
| Max | 21.27 | 20.53 | 30.15 | 43.47 |
| S D | 0.6611 | 1.5134 | 3.8894 | 8.6674 |
| Brain | 1.6525 | 1.1933 | 0.8908 | 0.7237 |
| Min | 1.56 | 1.10 | 0.75 | 0.71 |
| Max | 1.73 | 1.32 | 1.05 | 0.75 |
| S D | 0.0916 | 0.1161 | 0.1483 | 0.0232 |
| Heart/Blood | 1.0776 | 1.1490 | 1.0809 | 1.0408 |

-continued

Distribution of Radioactivity in Rat Tissues at Various Times after Intravenous Administration of [$^{125}$I]-Methyl-2-Deoxy-2-(E)~Iodovinyl-2,4,6-O~Triacetyl-β-D-Altropyranoside

|  | 5 MIN | 15 MIN | 30 MIN | 1 HT/R |
|---|---|---|---|---|
| Min | 1.06 | 1.08 | 1.06 | 1.01 |
| Max | 1.09 | 1.23 | 1.10 | 1.07 |
| S D | 0.0129 | 0.0739 | 0.0178 | 0.0292 |
| Brain/Blood | 1.5666 | 1.2775 | 1.1035 | 1.1087 |
| Min | 1.49 | 1.20 | 1.01 | 1.10 |
| Max | 1.64 | 1.39 | 1.18 | 1.12 |
| S D | 0.0594 | 0.0990 | 0.0838 | 0.0107 |

In human applications, the radiopharmaceutical is combined with a saline solution or another suitable administering medium and is given to the subject by intravenous injection. Only a trace amount of the radiopharmaceutical is needed, the preferred amount being dependant on the extent of specific activity desired. Normally, one would want an amount sufficient to provide a distinct image, the exact amount depending on a number of factors that can be readily determined by persons skilled in the art.

The radioiodinated iodovinyl substituted carbohydrates offer advantages over fluorine-18 and carbon-11 labeled glucose analogues that have been previously used for measuring regional glucose metabolism in the brain and heart, since radioiodine is a single photon emitter with a 13.3 hour half-life making it detectable using widely available single photon emission computerized tomographic devices. It is also easily prepared following the process of this invention. Other carbohydrates that have advantages similar to glucose could also be synthesized. One such carbohydrate is mannose which could provide radiopharmaceuticals that exhibit activity in specific body tissues.

We claim:

1. A stabilized iodinated branched carbohydrate comprising: a branched carbohydrate to which is attached a vinyl functional group to which is attached an iodine molecule.

2. A compound of claim 1 wherein said iodine is radioisotope I-123.

3. A compound of claim 1 wherein said branched carbohydrate is a glucose analogue and said vinyl functional group is attached at position-two carbon of said glucose analogue.

4. A compound of claim 3 having the structure

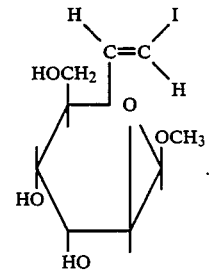

5. A compound of claim 4 wherein said iodine is radioisotope I-123.

6. A compound of claim 3 having the structure

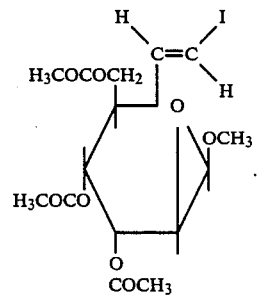

7. A compound of claim 3 wherein said iodine is radioisotope I-123.

* * * * *